(12) United States Patent
Mikulásik et al.

(10) Patent No.: US 10,441,660 B2
(45) Date of Patent: Oct. 15, 2019

(54) PHARMACEUTICAL PREPARATIONS CONTAINING HIGHLY VOLATILE SILICONES

(71) Applicant: EGIS GYOGYSZERGYAR NYILVANOSAN MUKODO RESZVENYTARSASAG, Budapest (HU)

(72) Inventors: Endre Mikulásik, Alsonemesapati (HU); Patrik Fazekas, Körmend (HU)

(73) Assignee: EGIS GYOCYSZERGYAR NYILVANOSAN MUKODO RESZVENYTARSASAG, Budapest (HU)

( * ) Notice: Subject to any disclaimer, the term of this patent is extended or adjusted under 35 U.S.C. 154(b) by 0 days.

(21) Appl. No.: 15/688,728

(22) Filed: Aug. 28, 2017

(65) Prior Publication Data

US 2018/0071395 A1    Mar. 15, 2018

Related U.S. Application Data

(62) Division of application No. 12/672,696, filed as application No. PCT/HU2008/000083 on Jul. 10, 2008, now Pat. No. 9,775,908.

(30) Foreign Application Priority Data

Jul. 10, 2007    (HU) .................... 0700473

(51) Int. Cl.
| | | |
|---|---|---|
| *A61K 47/34* | (2017.01) | |
| *A61K 31/5415* | (2006.01) | |
| *A61K 31/495* | (2006.01) | |
| *A61K 31/4174* | (2006.01) | |
| *A61K 9/06* | (2006.01) | |
| *A61K 47/02* | (2006.01) | |
| *A61K 31/4164* | (2006.01) | |

(Continued)

(52) U.S. Cl.
CPC ............. *A61K 47/34* (2013.01); *A61K 9/06* (2013.01); *A61K 31/4164* (2013.01); *A61K 31/4174* (2013.01); *A61K 31/495* (2013.01); *A61K 31/5415* (2013.01); *A61K 47/02* (2013.01); *A61K 9/0014* (2013.01); *A61K 9/1611* (2013.01)

(58) Field of Classification Search
None
See application file for complete search history.

(56) References Cited

PUBLICATIONS

Declaration of Endre Mikulásik from U.S. Appl. No. 12/672,696, Jun. 16, 2014. (Year: 2014).*

(Continued)

*Primary Examiner* — Bethany P Barham
*Assistant Examiner* — Dominic Lazaro
(74) *Attorney, Agent, or Firm* — Knobbe, Martens, Olson & Bear, LLP

(57) ABSTRACT

The subject of the present invention is a transdermal preparation containing pharmaceutically active ingredient, wherein the particles of the active ingredient are coated with highly volatile silicones or a mixture thereof, and these coated particles are dispersed in a gel or cream base. The volatile silicone component is hexamethyldisiloxane and/or octamethyltrisiloxane and/or decamethylpentacyclo-siloxane. A further subject of the present invention is a method for the preparation of such pharmaceutical compositions.

10 Claims, 11 Drawing Sheets

(51) Int. Cl.
　　　*A61K 9/00*　　　(2006.01)
　　　*A61K 9/16*　　　(2006.01)

(56) References Cited

PUBLICATIONS

Declaration of Dr. Zoltán Varga from U.S. Appl. No. 12/672,696, Mar. 3, 2017. (Year: 2017).*

* cited by examiner

PHARMACEUTICAL PREPARATIONS CONTAINING HIGHLY VOLATILE SILICONES

The subject of the present invention is a transdermal preparation containing a pharmaceutically active ingredient, wherein the particles of the active ingredient are coated with highly volatile silicones or a mixture thereof and these coated particles are dispersed in a gel or cream base. A further subject of the present invention is a method for the preparation of such pharmaceutical compositions.

The application of the silicone derivatives in medicine started in the 1930's and since then they have been applied extensively.

As to the group of silicone derivatives, the application of silicone polymers are really widespread in the field of pharmaceutics, because they have several advantageous characteristics, such as high flexibility, heat-resistance, beneficial chemical resistance, they are indifferent to the human organism, they have no interaction with it in the course of pharmaceutical application.

Silicone polymers—polyorganosiloxanes—are polymer compounds, wherein organic chemical groups are attached to the siloxane chains (—Si—O—Si—).

By the hydrolysis or condensation of chlorosilane monomers different silicone polymers can be prepared. These polymers have three main groups depending on their structures:

silicone oils and natural elastomers with linear structure,
silicone resins with branched structure,
silicone resins with cross-linked structure (most of the silicone resins have cross-linked structure).

Not only silicone oils with different degree of viscosity but also fat silicones, antifoams, form release agents and hydrophobizing agents can be prepared from the silicone polymers. Silicone rubbers are prepared from silicon caoutchoucs by different vulcanizing and cross-linking processes.

Resins can be used as pressing powders, pressing resins, resin emulsions, lacquers (solutions with different solvents) and pigmented paints or resins modified with organic components.

Silicone polymers are important basic materials of the pressure sensitive adhesives (PSA), medicinal and surgical implants, prostheses used in the therapy and different transdermal therapeutic systems (TTS).

Among the silicone oils dimethyl polysiloxanes are applied most often in the therapy. These silicone oils have very strong antifoaming properties, which arise from their low surface tension (approximately 20 mN/m, for comparison the surface tension of water is 85 mN/m). This advantage is employed by the application of silicone oil in sprays for the treatment of lung oedema. In case of lung oedema the strongly foamy mucus originating from the lung and making a barrier in the normal ventilation and in the oxygen uptake can cause anoxia or suffocation in lack of treatment. The hydrophobic characteristics of silicone oils are used in pharmaceutical preparations for the treatment of bedsore and ulcer with patients who have to stay in a single decubitus position for a lengthy period.

One sub-group of silicone oils are the highly volatile silicones. The highly volatile silicones are pharmaceutical carriers which are able to evaporate completely from the surface of the human skin within 6 hours. The pharmaceutical use of these carriers has not been exhausted every possibility, yet.

The subject of the present invention is a pharmaceutical transdermal preparation, wherein the particles of the active ingredient are coated with hexamehyldisiloxane, octamethyltrisiloxane and decamethylpentacyclosiloxane. These highly volatile silicone oils are widely used in the cosmetics industry and their pharmaceutical application is also known.

U.S. Pat. Nos. 4,355,046 and 5,336,692 describe the use of hexamethyldisiloxane, octamethyltrisiloxane and decamethylpentacyclosiloxane solvents in ointments having a petrolatum base. The ointments are applied in cosmetics and medicine. According to these patents highly volatile siloxanes serve exclusively in order to obtain a good distribution on the surface of the human skin, but not to attain chemical and microbiological stability. The type and the composition of the pharmaceutical preparations and also the ointment base cited in the descriptions are different from the subject of the present invention. In U.S. Pat. No. 5,210,103 hexamethyldisiloxane is used as power gas in skin foams for external use (for example: vaginal).

European Patent No. EP 914082 relates to an antiperspirant composition containing volatile siloxanes. These silicones assure the suitable consistency of the composition and avoid any leakage of the product from the packaging.

By the production of Diprolene Creme® (Schering Plough) and Dexeryl Creme® (Pierre Fabre Sante) decamethylpentacyclosiloxane is used to assure the aesthetics of the product.

All of the above cited documents describe cosmetic compositions wherein the volatile siloxanes are used to assure the suitable consistency of the compositions and the aesthetics of the products.

Volatile siloxanes are rarely applied in pharmaceutical compositions as ingredients. The composition of the pharmaceutical preparations cited in the literature are different from the subject of the present invention, and in the pharmaceutical compositions of the state of the art, similarly to the cosmetic products, volatile siloxanes serve to obtain a good distribution on the surface of the skin.

At the same time in the present invention volatile silicone oils assure chemical and microbiological stability and good bioavailabilty to our composition.

The basic requirements of pharmaceutical ointments and creams containing an active ingredient are good stability, long storage time, suitable penetration of the active substance from the transdermal system, good consistency and easy application to the skin.

A disadvantage of the ointments having fatty or oily bases is that the penetration of the active ingredient is slow and the amount of the released active substance is low, because in the lipophil phase the solubility of the ointment is higher, especially in case of active substances having low aqueous solubility, and therefore, the distribution is not equal, the ointment base contains more active substance. Examples of active ingredients with low aqueous solubility are aciclovir, piroxicam, meloxicam, ibuprofen, diclofenac sodium and potassium salt, clotrimazol, bifonazol, metronidazol, nifedipin, nitroglycerin and cetirizin. Examples for creams containing the above active ingredients are Zovirax® (aciclovir), Feldene® (piroxicam), Hotemin® cream (piroxicam), Canesten® cream (clotrimazol), Mycospor® cream (bifonazol) or Rozex® cream (metranidazol).

Gel compositions containing the active ingredient in a suspended form are known from the literature, wherein the release of the active substance is adequate, but stability problems can occur during storage. These problems are caused by the chemical and microbiological reactions on the contact areas of the different surfaces, which may change the chemical condition of the active substance. These kind of stability problems can occur for example during the storage of Hotemin® cream containing piroxicam, Voltaren® emulgel (diclofenac) or Rozex® gel containing metronidazol.

The aim of the present invention is to develop a pharmaceutical preparation having better bioavailabilty than the ointments having fatty or oily bases and some gels and also to avoid stability problems occurring during the storage of emulgels or gels containing the active substance in suspended form.

Surprisingly, it has been found that the above aims can be reached by a pharmaceutical preparation wherein volatile silicon oils are used as adjuvants. To improve the stability and penetration properties of the ointments and gels containing the above mentioned active ingredients, we used mixtures of silicone oils with different volatility in properly selected ratios.

The subject of the present invention is a transdermal preparation containing a pharmaceutically active ingredient, wherein the particles of the active ingredient are coated with highly volatile silicones or a mixture thereof and these coated particles are dispersed in a gel or cream base.

The pharmaceutical preparation of the present invention contain aciclovir, piroxicam, meloxicam, ibuprofen, diclofenac sodium and diclofenac potassium salt, clotrimazol, bifonazol, metronidazol, nifedipin, nitroglycerin or cetirizin as active ingredients; hexamethyldisiloxane and/or octamethyltrisiloxane and/or decamethylpentacyclosiloxane as volatile siloxane adjuvants; carboxyvinyl polymer, hydroxypropyl-methylcellulose or a mixture thereof as ointment bases.

A further subject of the present invention is a method for the preparation of such pharmaceutical compositions by coating the particles of the active ingredient with highly volatile silicones or a mixture thereof and the obtained mixture is dispersed in a gel or cream base, thus the particles in the gel or cream base are surrounded by silicone coating.

The essence of the invention is that the solid particles of the active ingredient incorporated in the gel are coated with volatile silicon oils, which evaporate from the surface of the skin in the course of use. The active substance and the other ingredients of the gel remain on the surface of the skin and adsorb fast through the physiological transport systems (diffusion, penetration, permeation) of the skin.

Stability can be increased with the silicone coating, which forms a so-called "third phase" in the gels. This "third phase" interacts neither with the active ingredient, nor with the other adjuvants of the gel. Silicone oils form a coating around the active ingredient particles, which protects the active ingredient from chemical and microbiological impacts assuring the pharmaceutical composition good chemical and microbiological stability.

Applying the gel to the skin the silicone compound evaporates, thus it does not have any interaction with the human organism. The particles of the active ingredients remain on the surface of the skin and release in the body. After the evaporation of the adjuvant, the active substance particles can release easier and more effectively into the layers of the skin.

The most appropriate silicon oils for coating the active ingredient of the transdermal composition of the present invention are hexamethyldisiloxane, octamethyltrisiloxane and decamethylpentacyclosiloxane.

The advantageous properties of the pharmaceutical composition of the present invention are demonstrated by the following experiments:

DESCRIPTION OF THE FIGURES

FIG. 5 shows the released percentage of the active ingredient comparing to the whole amount in case of the two compositions.

FIG. 6 demonstrates the released amount of the active substance on a certain surface of the skin in $mg/cm^2$ in case of the two compositions.

FIG. 10 demonstrates the released amount of the active substance on a certain surface of the skin in $mg/cm^2$ in relation the half time of the diffusion. (Q root (t))

CHEMICAL STABILITY TEST

One of the chemical stability problems of the gel type pharmaceutical formulations containing active substance in dispersed form is caused by the reactions occurring at the contact points of the surfaces, which can lead to the change of the chemical condition of the active ingredient.

The polymorph form I of piroxicam is a white substance with crystalline structure, which turns into a bright yellow colour when dissolved in water or in other solvents. In case of traditional ointments and gels containing this active substance, the above described chemical reactions change the intensity of colour of the pharmaceutical preparation.

It has been found that contrary to the cream and gel formulations of the state of the art, the colour of the aqueous gel of the present invention containing the active ingredient coated with volatile silicone oils (hexamethyldisiloxane and/or octamethyltrisiloxane, or a mixture thereof in a ratio of 1:1) does not change. The pharmaceutical preparations of the present invention were examined with stability tests complying with the current ICH (International Conference on Harmonisation of Technical Requirements for the Registration of Pharmaceuticals for Human Use) rules, and the white colour of the preparations did not change during the experiments.

The active ingredient is coated with the volatile silicon oils in a manner that the other ingredients of the gel formulation do not have contact with the active ingredient as a result of which the preparation has good chemical stability.

Experiments for Mass Decrease

A basic requirement of good bioavailability is that the active substance should have a good release from the pharmaceutical preparation. The active ingredient of the composition of the present invention releases after the evaporation of the silicon oils serving as a coating. This process is shown by the weight decrease of the preparation. As a reference we used Hotemin® cream which is a cream with a fatty basis.

The ingredients of Hotemin® cream 1% are: methyl parahydroxybenzoate, macrogol cetylstearyl ether, sorbitan stearate, stearic acid, cetyl stearil alcohol, white vaseline, liquid paraffin, purified water.

Figure 1:
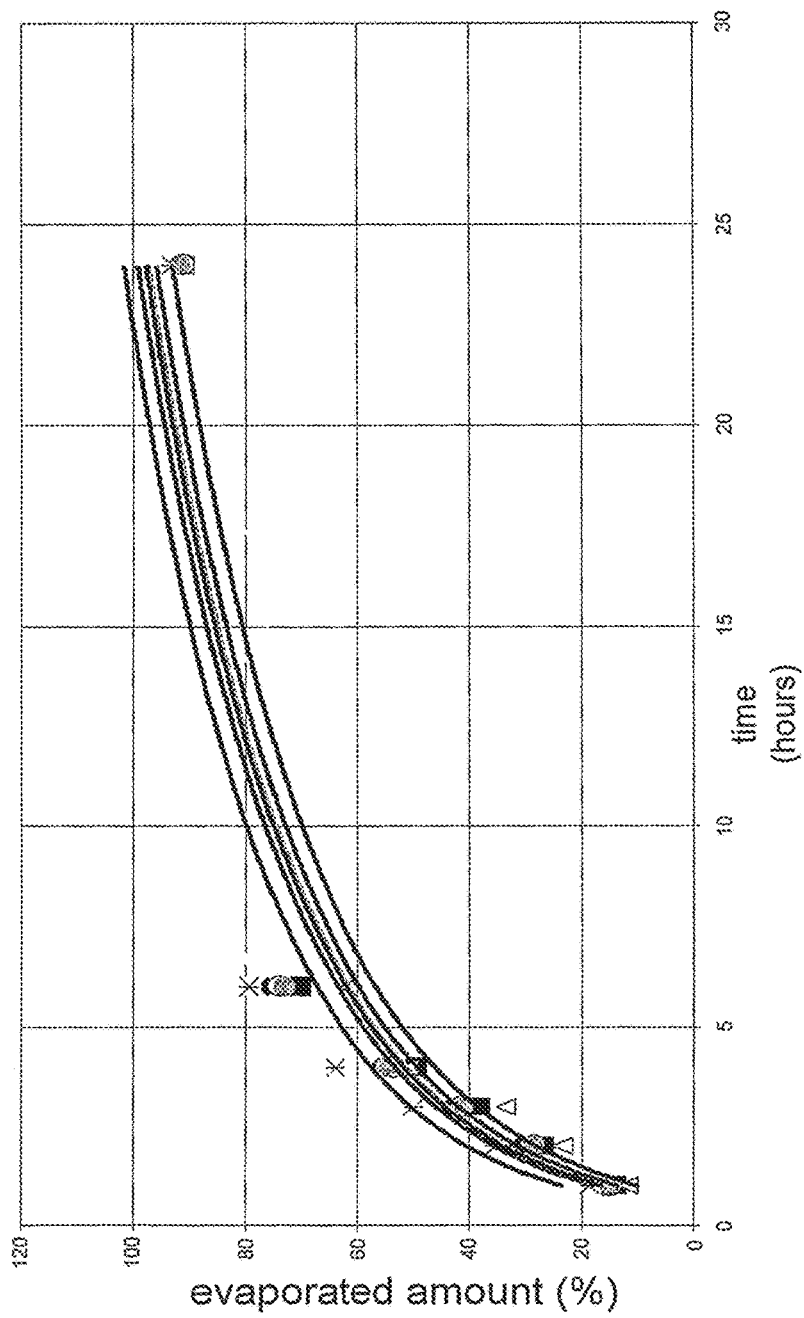
FIG. 1 demonstrates the kinetics of evaporation from silane containing system, which was studied in the mass decrease experiments. 5 samples were stored in a standard humidity exsiccator and were measured on analytical scales at certain intervals. The results of 5 measurements are demonstrated by the curves. Black pots indicate the curve demonstrating the mean value.
Figure 2:
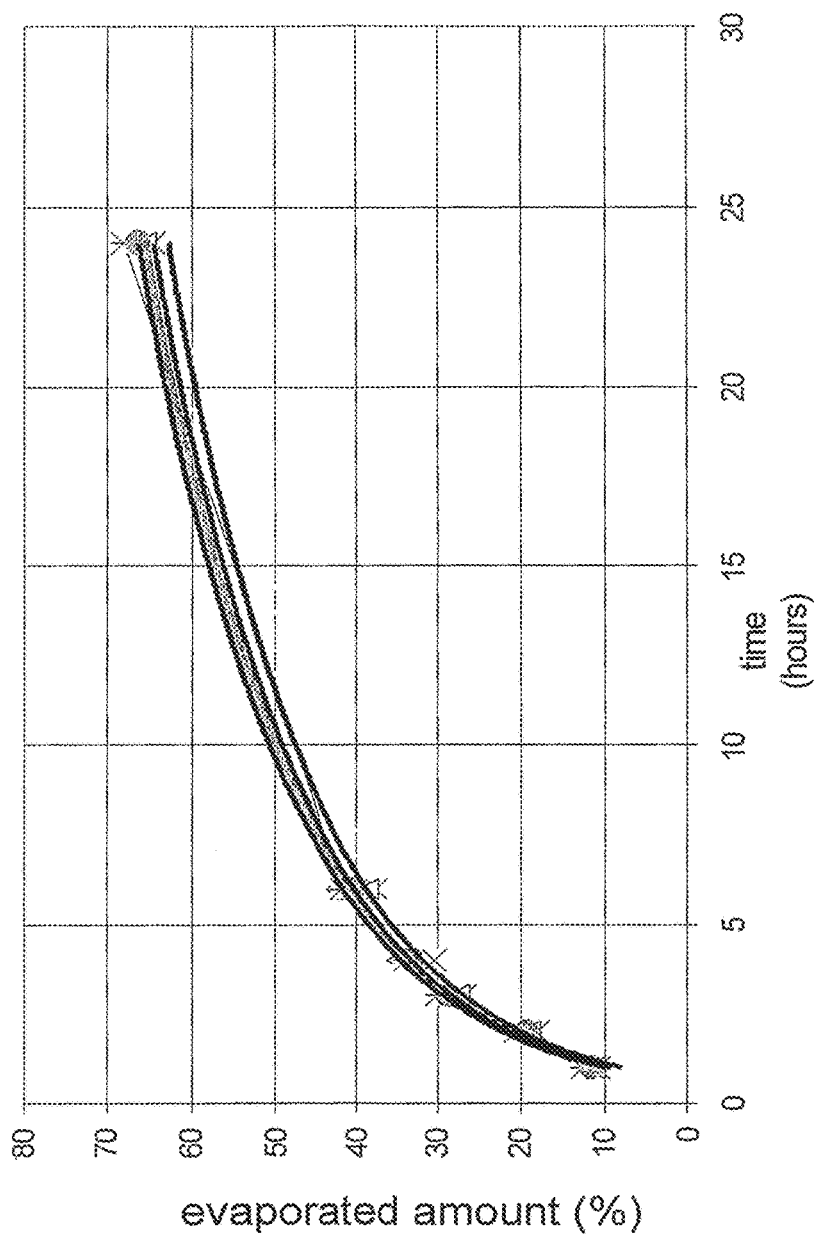
FIG. 2 demonstrates the kinetics of evaporation from silane containing system, which was studied in the mass decrease experiments. 3 samples were stored in a standard humidity exsiccator and were measured on analytical scales at certain intervals. The results of 3 measurements are demonstrated by the curves. Black pots indicate the curve demonstrating the mean value.

The samples were stored in a standard humidity exsiccator and they were measured on analytical scales at certain intervals. FIGS. 1 and 2 demonstrate the mass decrease and its relation to time.

The results of the measurements show that the evaporation is faster from the system containing the volatile silicones than from the reference preparation. After 24 hours only the active ingredient and a small amount of the polymer adjuvant remained on the scales. The reference ointment had lower mass decrease; only the 60% of the whole mass evaporated.

Experiments Concerning the Transport Through the Biological Membranes

Another basic condition of good bioavailability is the easy diffusion of the active substance after release through the biological membrane by active or passive transport.

The transport of the active ingredient through apolar and semipolar biological membranes (for example: skin) was studied with the help of an apparatus operating according to the operation principle of the vertical diffusion cell developed by the Hanson Company (Hanson Microette TM Topical & Transdermal Diffuson Cell System, Hanson Research Corporation).

The reference composition of the experiments is Hotemin® ointment.

Diffusion Through Apolar Membrane

Diffusion through apolar membrane was studied because the upper layer of the skin, the stratum corneum, has a lipophil, apolar character because of the chemical characteristics of its components. Therefore, first of all pharmacones having the ability of dissolving in the stratum corneum are able to get into it as well as the drugs which have apolar characteristics.

Figure 3:
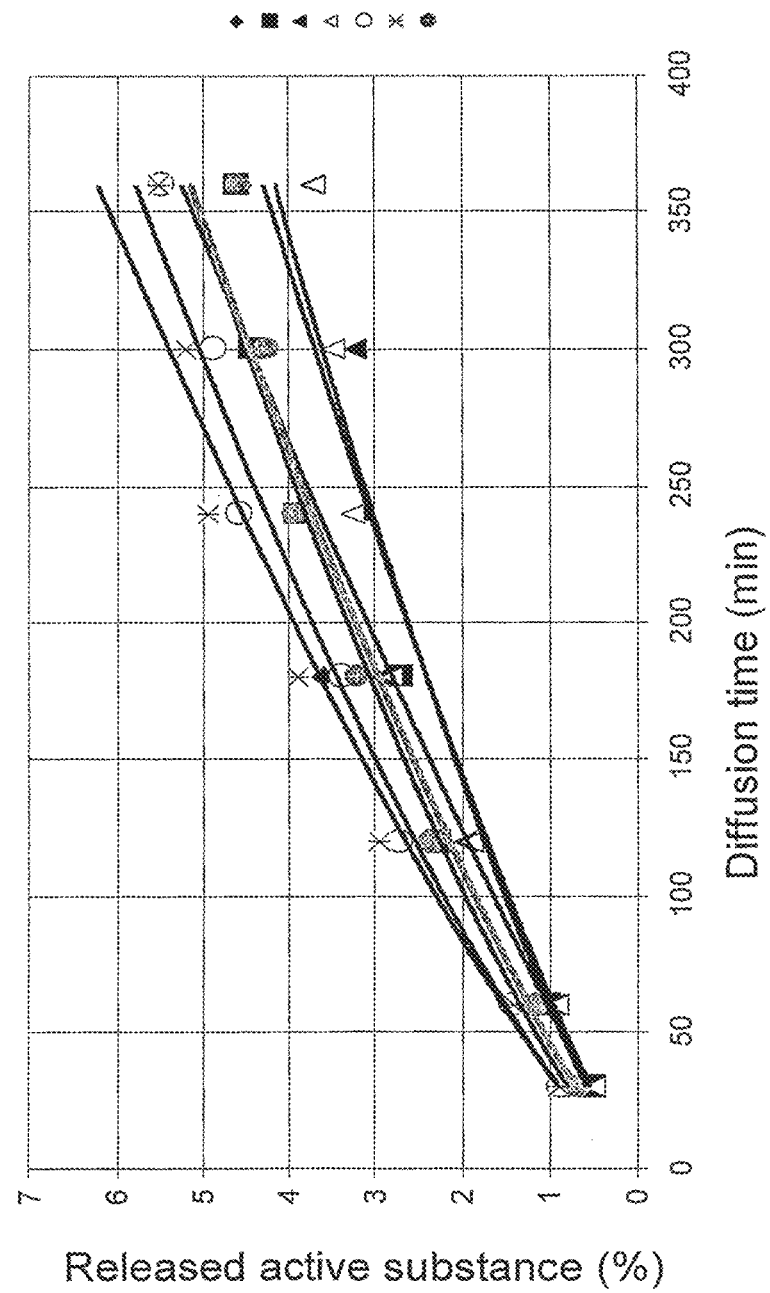
FIG. 3 relates to the release of piroxicam from the silane composition through a lipophil membrane. The results of the diffusion experiments through apolar membrane are demonstrated here. Black pots indicate the curve demonstrating the mean value of 6 measurements.

FIG. 3 shows the results of the experiments carried out using a membrane impregnated with isopropyl myristate.

Figure 4:
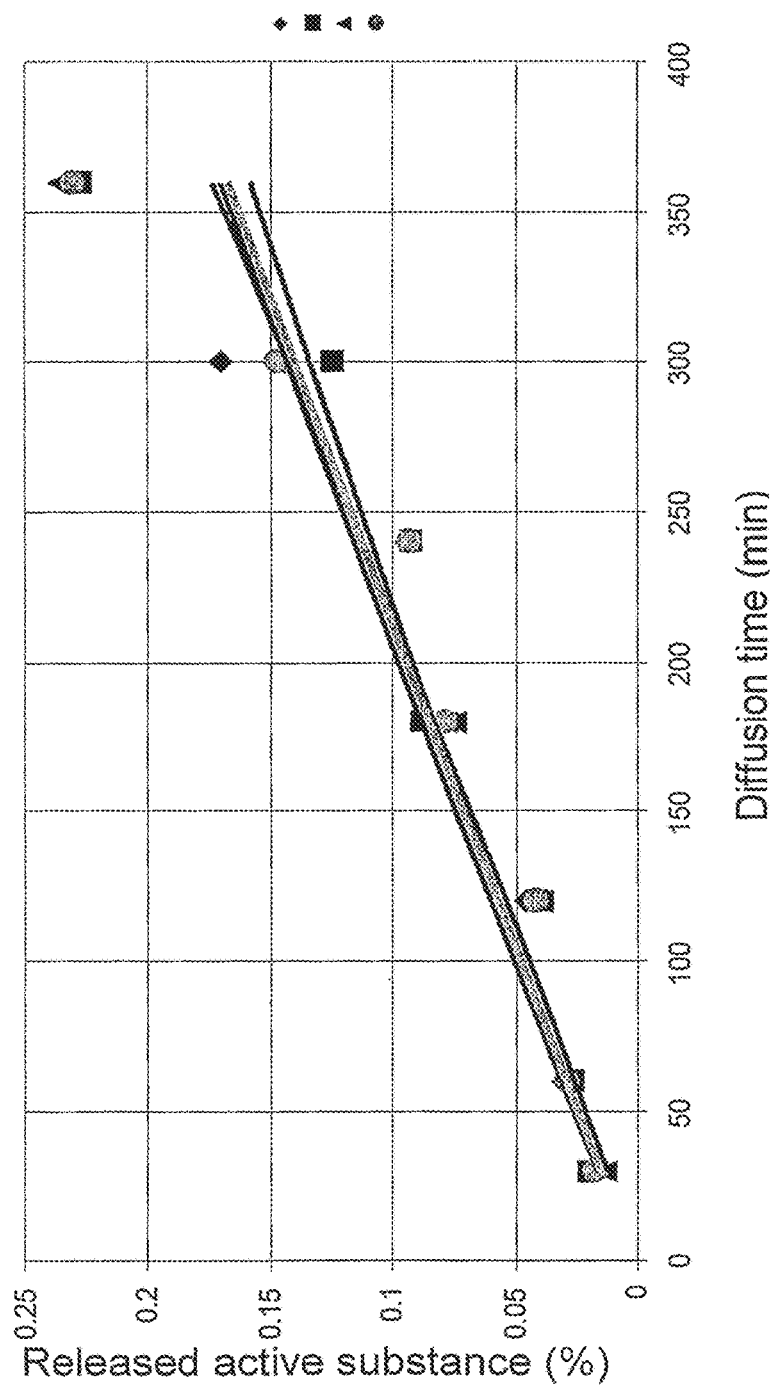
FIG. 4 relates to the release of piroxicam from Hotemin® ointment through a lipophil membrane. The results of the diffusion experiments through apolar membrane are demonstrated here. Black pots indicate the curve demonstrating the mean value of 3 measurements.
Figure 5:
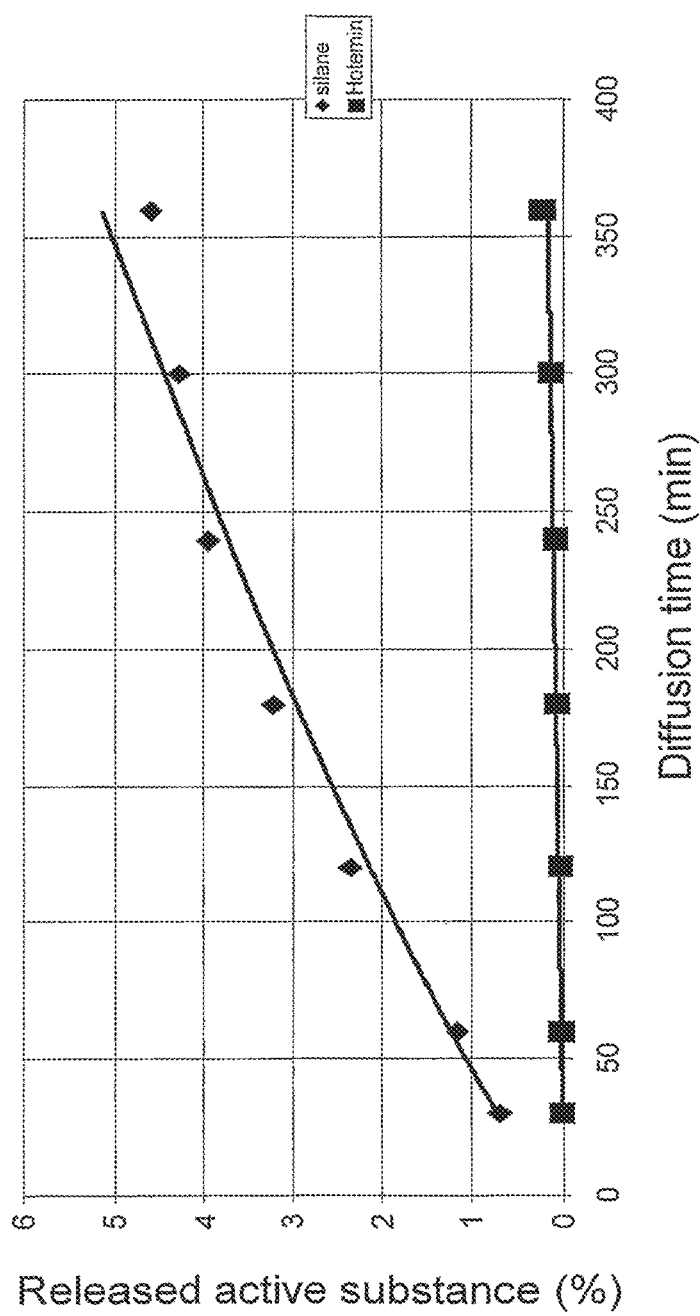
FIG. 5 relates to a comparative test, which demonstrates the release of piroxicam from silane system and from Hotemin® cream through a lipophil membrane.
Figure 6:
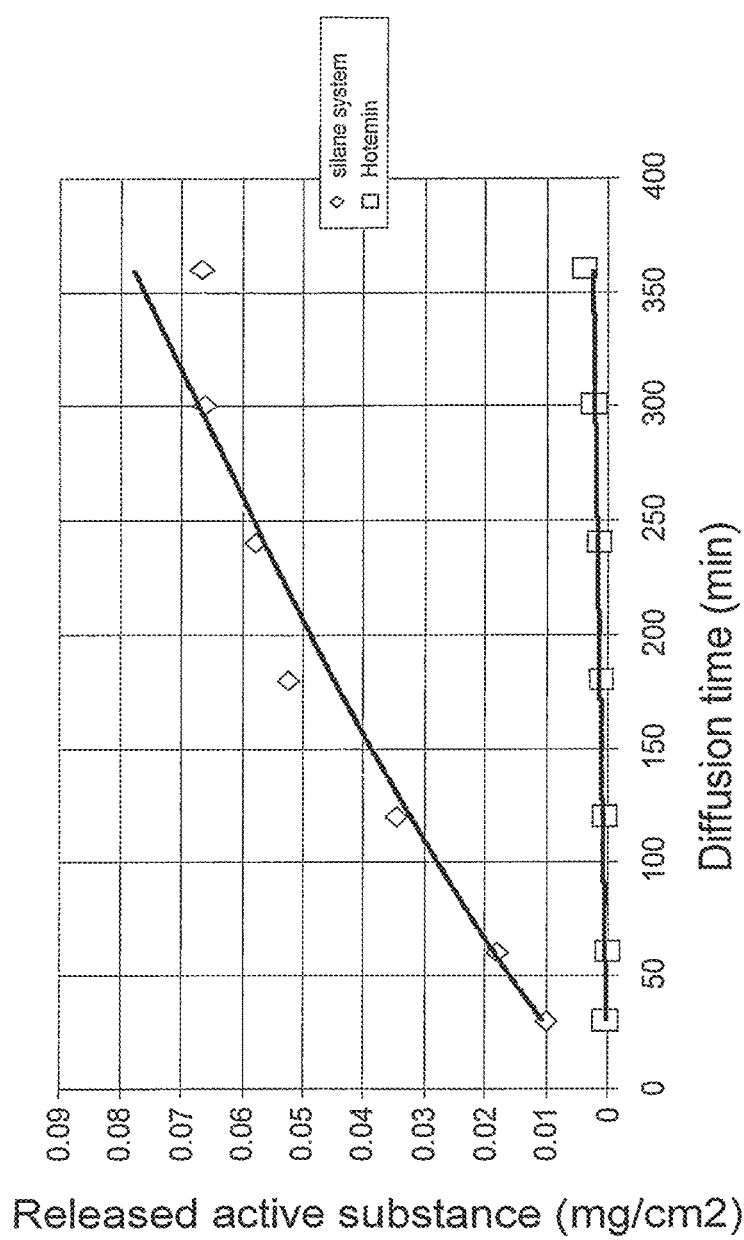
FIG. 6 relates to a comparative test, which demonstrates the release of piroxicam from silane system and from Hotemin® cream through a lipophil membrane.
Figure 7:
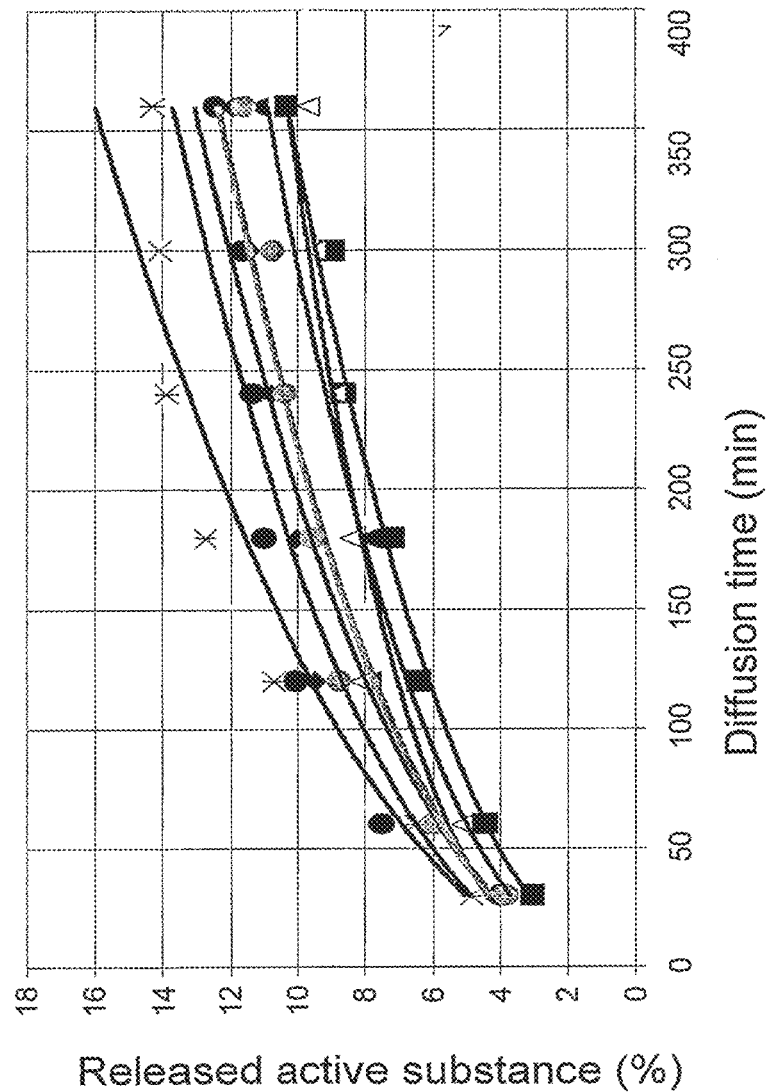
FIG. 7 relates to the release of piroxicam from the silane composition through a semipolar membrane. The results of the diffusion experiments through semipolar membrane are demonstrated here. Black pots indicate the curve demonstrating the mean value of 5 measurements.
Figure 8:
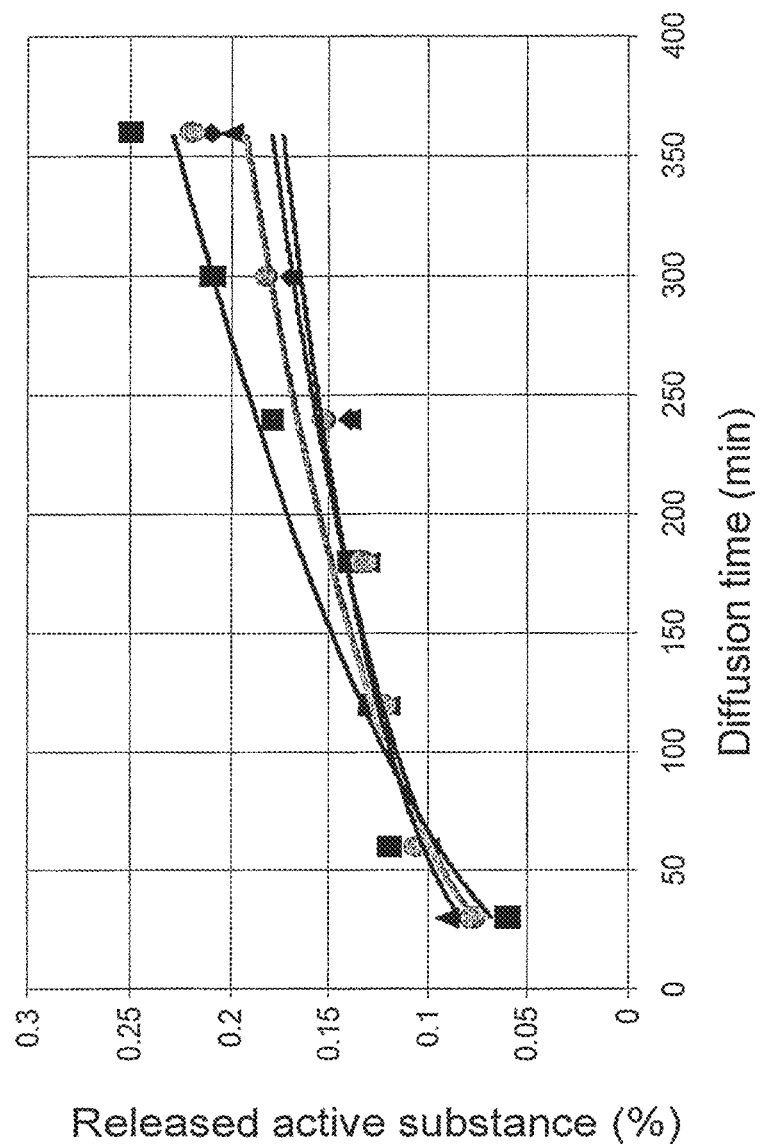
FIG. 8 relates to the release of piroxicam from Hotemin® ointment through a semipolar membrane. The results of the diffusion experiments through semipolar membrane are demonstrated here. Black pots indicate the curve demonstrating the mean value of 3 measurements.
Figure 9:
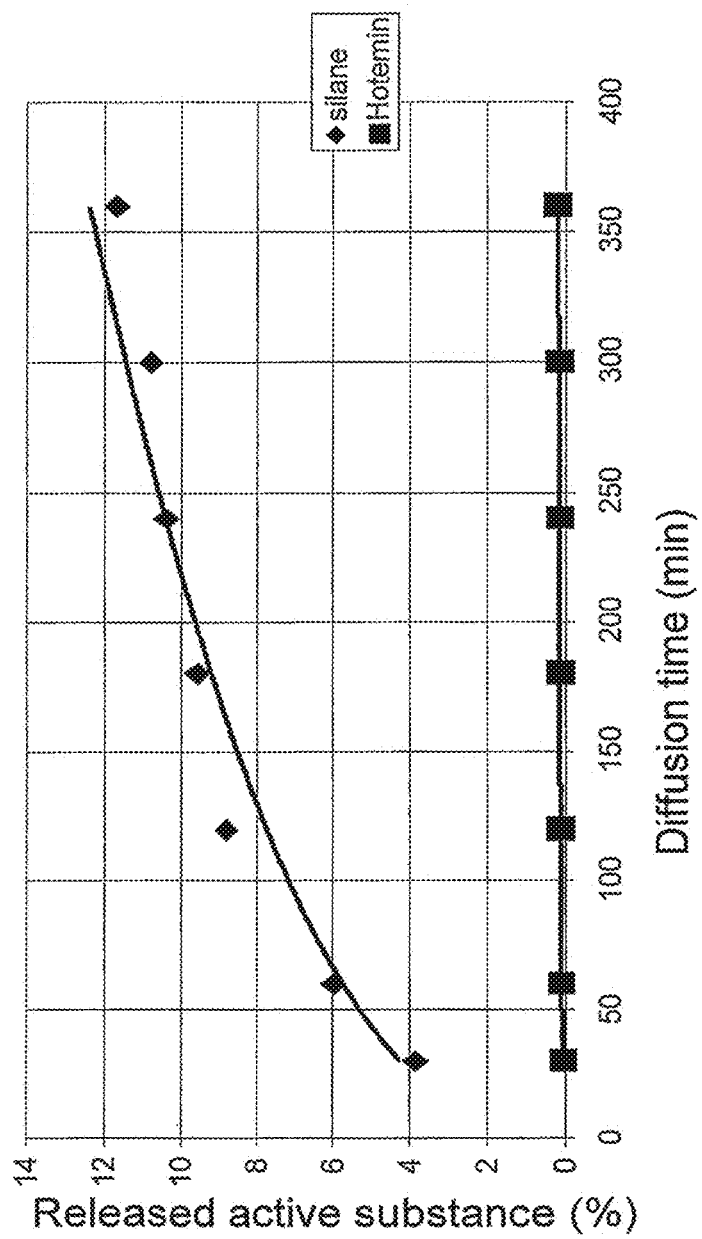
FIG. 9 relates to a comparative experiment, which demonstrates the release of piroxicam from the "silane system" and Hotemin® composition through a semipolar membrane.

FIG. 4 demonstrates the release of the reference composition and FIGS. 5 and 6 are comparative examples.

FIG. 5 shows the released percentage of the active ingredient comparing to the whole amount and FIG. 6 demonstrates the released amount of the active substance on a certain surface of the skin in mg/cm$^2$.

Usually the process taking place in time is described with a root function. The general formula of the root function is:

$$Q = Q_0 t^m \quad (1),$$

wherein Q represents the released amount of the active ingredient during t time, $Q_0$ represents the released amount of the active ingredient at t=0 (it is usually 0) and m represents the gradient of the linearized function. If m is 1, the amount of the released active ingredient increases linearly in time, but usually m has a lower value than 1. When m is approximately 0.5, Q is shown by a linear function at $t_{0.5}$ function. The gradients of the linears (angular coefficient) are the velocity constant of the release.

Evaluating the functions mathematically it can be stated that the root function of equation (1) can be exactly matched to the measurement points. Table 1 shows the constant of $Q_0$, m and $R^2$ which represents the degree of the regression.

TABLE 1

The kinetics of the release of piroxicam. The constants of the root function matched to the measurement points and the values of the correlation coefficient

| Experiment No. | $Q_0$ | m | $R^2$ |
| --- | --- | --- | --- |
| Silicone containing system | | | |
| Measurement 1 | 0.061 | 0.754 | 0.982 |
| Measurement 2 | 0.025 | 0.909 | 0.986 |
| Measurement 3 | 0.039 | 0.791 | 0.973 |
| Measurement 4 | 0.031 | 0.839 | 0.979 |
| Measurement 5 | 0.069 | 0.752 | 0.994 |
| Measurement 6 | 0.063 | 0.779 | 0.984 |
| mean value | 0.047 | 0.798 | 0.988 |
| Reference composition | | | |
| Measurement 1 | 0.0006 | 0.948 | 0.934 |
| Measurement 2 | 0.0007 | 0.927 | 0.926 |
| Measurement 3 | 0.0003 | 1.065 | 0.953 |
| mean value | 0.0005 | 0.975 | 0.945 |

The values of Table 1 show that the kinetics of the process is described precisely by the root function. The value of $Q_0$ is around 0, the value of m is between 0.5 and 1, therefore the process is not linear in time, but the velocity of the process is continuously decreasing. The root transformation was not carried out as the value of m is different from 0.5.

During the six-hour long experiment the release of the active ingredient from sample containing silicone oil was approximately 5%. From the reference composition less than 1% was released during the experiment (the maximum release of the active was approximately 0.2%).

As to the results of our experiments it can be concluded that the composition prepared according to the present invention is able to release much more of the active ingredient than the reference composition.

Diffusion Through Semipolar Membrane

The experiments of transport through a semipolar membrane gives a model of entering into the living cell, and passing through the living cell, which is a condition of the pharmacological efficacy.

The semipolar membrane was prepared by impregnating it with ethyl alcohol. The results of our experiments are demonstrated by FIGS. 7-10.

Comparing the Release of the Active Ingredients of the Composition of the Present Invention and Hotemin® Ointment:

Studying the kinetics of the process, it has been found that value m is ~0.5 of the equation (1), therefore the root transformation was carried out. The results demonstrated by FIG. 11 and the $R^2$ values of the regression line show a close match. Table 2 shows the values of $Q_0$, m and $R^2$.

TABLE 2

The release of the active ingredient through a semipolar membrane

| Experiment No. | $Q_0$ | m | $R^2$ |
|---|---|---|---|
| Silicone containing system | | | |
| Measurement 1 | 0.932 | 0.449 | 0.945 |
| Measurement 2 | 0.644 | 0.471 | 0.994 |
| Measurement 3 | 0.843 | 0.435 | 0.894 |
| Measurement 4 | 1.032 | 0.465 | 0.961 |
| Measurement 5 | 1.369 | 0.343 | 0.949 |
| Measurement 6 | 1.191 | 0.415 | 0.895 |
| mean value | 0.990 | 0.429 | 0.962 |
| Reference composition | | | |
| Measurement 1 | 0.024 | 0.340 | 0.923 |
| Measurement 2 | 0.013 | 0.494 | 0.922 |
| Measurement 3 | 0.031 | 0.249 | 0.903 |
| mean value | 0.021 | 0.373 | 0.941 |

The ratio between the composition containing silicon and the reference Hotemin® ointment is 50:1, namely the amount of the released active ingredient is fifty fold more than the released amount of the active ingredient from the reference composition.

Comparing the Release of the Active Ingredients of the Composition of the Present Invention and Other Transdermal Pharmaceutical Preparations Containing Piroxicam:

The diffusion of the composition of the present invention through a semipolar membrane was compared with the following preparations:

Erazon® 1% cream,
Erazon® 1% gel,
Feldene® 0.5% gel,
Feldene-top Creme®,
Hotemin® ointment.

The above compositions contain piroxicam, but the carriers and the ingredients thereof are different from the composition of the invention.

It has been discovered that the release of the active ingredient from the composition containing volatile silicones is greater than the above examined creams and gels. (See FIG. 11.)

The pharmaceutical composition of the invention is further elucidated by means of the following Examples without restricting the scope of the present invention to the examples.

In the examples Silicon Fluid carriers are methylsiloxanes, namely hexamethyldisiloxane and/or octamethyltrisiloxane, or the mixtures thereof in a ratio of 1:1. In the examples the viscosity of the siloxane solutions is 0.65 cSt or 100 cSt.

EXAMPLES

Example 1

Gel Composition Containing Piroxicam as Active Ingredient:

| | |
|---|---|
| Piroxicam | 0.500 g |
| Silicone fluid 0.65 cSt | 0.500 g |
| Silicone fluid 100 cSt | 2.150 g |
| Carbopol 980 NF | 0.250 g |
| Triethanolamine | 0.200 g |
| Hydroxypropyl-methylcellulose | 1.000 g |
| Purified water | ad 50.000 g |

According to the recipe of the above example the gel was prepared in a batch size of 7 kg with a Brogtech apparatus suitable for the preparation of ointments.

1.1. Method of Preparation of the Suspension Containing the Active Ingredient:

Micronized piroxicam powder (70.0 g) is mixed with Silicone fluid 0.65 cSt (301.0 g) and Silicone fluid 100 cSt (70.0 g) in an 800 ml beaker glass, and the mixture in an Ultra-Turrax apparatus, at 4000 revs/minute for 5 minutes. The prepared suspension is stored in an airtight place until application.

1.2. Method of Preparation of the Gel Base:

Purified water (6000 g) is poured into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) is added to the reaction mixture and it is stirred for 4 hours. The mixture is neutralized with a solution of triethanolamine (28.0 g) and purified water (100.0 g) and stirring is continued until the mixture has gel consistency.

1.3. Method of Preparation of the End Product (Drug-Gel Composition):

To the gel base prepared according to point 1.2, the suspension of the drug obtained according to point 1.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm).

Example 2

Gel Composition Containing Clotrimazol as Active Ingredient:

| | |
|---|---|
| Clotrimazol | 0.200 g |
| Silicone fluid 0.65 cSt | 1.000 g |
| Silicone fluid 100 cSt | 0.200 g |
| Carbopol 980 NF | 0.100 g |
| Triethanolamine | 0.200 g |
| Hydroxypropyl-methylcellulose | 0.400 g |
| Purified water | ad 20.000 g |

According to the recipe of the above example the gel was prepared in a batch size of 7 kg with a Brogtech apparatus suitable for the preparation of ointments.

2.1. Method of Preparation of the Suspension Containing the Active Ingredient:

Micronized clotrimazol powder (70.0 g) is mixed with Silicone fluid 0.65 cSt (350.0 g) and Silicone fluid 100 cSt (70.0 g) in a 800 ml beaker glass, and the mixture is homogenized in an Ultra-Turrax apparatus, at a 4000 revs/minute for 5 minutes. The prepared suspension is stored in an airtight place until application.

2.2. Method of Preparation of the Gel Base:

Purified water (6000 g) is put into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) to the reaction mixture and it is stirred for 4 hours. The mixture is neutralized with a solution of triethanolamine (28.0 g) and purified water (100.0 g) and stirring is continued until the mixture has gel consistency.

2.3. Method of Preparation of the End Product (Gel Composition):

To the gel base prepared according to point 2.2, the suspension of the drug obtained according to point 2.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm).

Example 3

Gel Composition Containing Metranidazol as Active Ingredient:

| | |
|---|---|
| Metronidazol | 1.000 g |
| Silicone fluid 0.65 cSt | 2.000 g |
| Silicone fluid 100 cSt | 0.200 g |
| Carbopol 980 NF | 0.250 g |
| Triethanolamine | 0.200 g |
| Hydroxypropyl-methylcellulose | 0.400 g |
| Purified water | ad 20.000 g |

According to the recipe of the above example the gel was prepared in a batch size of 7 kg with a Brogtech apparatus suitable for the preparation of ointments.

3.1. Method of Preparation of the Suspension Containing the Active Ingredient

Micronized metronidazol powder (350.0 g) is mixed with Silicone fluid 0.65 cSt (700.0 g) and Silicone fluid 100 cSt (70.0 g) in a 800 ml beaker glass, and the mixture in an Ultra-Turrax apparatus, at a 4000 revs/minute for 5 minutes. The prepared suspension is stored in an airtight place until application.

3.2. Method of Preparation of the Gel Base:

Purified water (5500 g) is put into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) is added to the reaction mixture and it is stirred for 4 hours. The mixture is neutralized with a solution of triethanolamine (28.0 g) and purified water (100.0 g) and stirring is continued until the mixture has gel consistency.

3.3. Method of Preparation of the End Product (Gel Composition):

To the gel base prepared according to point 3.2, the suspension of the drug obtained according to point 3.1 is added stepwise, and the gel is completed to 7.00 kg with purified water. The obtained gel is homogenized for 5 minutes in the built-in homogenizer of the Brogtech apparatus at 1200 revs/min, at the maximum diameter of the gaps (1.5 mm). The obtained gel is stored in an airtight place or put into an airtight packaging (metal tube).

Example 4

Gel Composition Containing Cetirizin as Active Ingredient:

| | |
|---|---|
| Cetirizin | 0.200 g |
| Menthol | 0.200 g |
| Ethyl alcohol | 0.200 g |
| Silicone fluid 0.65 cSt | 1.000 g |
| Silicone fluid 100 cSt | 0.200 g |
| Carbopol 980 NF | 0.250 g |
| Triethanolamine | 0.200 g |
| Purified water | ad 20.000 g |

According to the recipe of the above example the gel was prepared in a batch size of 7 kg with a Brogtech apparatus suitable for the preparation of ointments.

4.1. Method of Preparation of the Suspension Containing the Active Ingredient:

Micronized cetirizin powder (70.0 g) is mixed with Silicone fluid 0.65 cSt (350.0 g) and Silicone fluid 100 cSt (70.0 g) in an 800 ml beaker glass, and the mixture is homogenized in an Ultra-Turrax apparatus, at a 4000 revs/minute for 5 minutes. The prepared suspension is stored in an airtight place until application.

4.2. Method of Preparation of the Menthol Solution:

Menthol (70.0 g) is dissolved in ethyl alcohol in a 300 ml beaker glass. It is stored airtight until utilization.

4.3. Method of Preparation of the Gel Base:

Purified water (6000 g) is poured into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) to the reaction mixture and it is stirred for 4 hours. The mixture is neutralized with a solution of triethanolamine (28.0 g) and purified water (100.0 g) and stirring is continued until the mixture has a gel consistency.

4.3. Method of Preparation of the End Product (Gel Composition):

To the gel base prepared according to point 4.2, the suspension of the drug obtained according to point 4.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm). The obtained gel is stored in an airtight place or put into an airtight packaging (metal tube).

What is claimed is:

1. A process for the preparation of a pharmaceutical composition comprising a plurality of particles of an active pharmaceutical ingredient dispersed in a gel or cream base, the process comprising the steps of:
    coating substantially all of the particles of active ingredient with a layer of highly volatile silicone or a mixture of highly volatile silicones;

mixing the coated particles of active ingredient with a gel or cream base;

wherein the layer of highly volatile silicone or mixture of highly volatile silicones substantially prevents contact between the active pharmaceutical agent and the gel or cream base at least until application; and wherein the mass ratio of the layer of highly volatile silicone or mixture of highly volatile silicones to the active pharmaceutical agent is at least about 2:1.

2. The process of claim 1, wherein the highly volatile silicone or mixture of highly volatile silicones is selected from the group consisting of hexamethyldisiloxane, octamethyltrisiloxane, decamethylpentacyclosiloxane and mixtures thereof.

3. The process of claim 1, wherein the highly volatile silicone or mixture of highly volatile silicones comprises hexamethyldisiloxane.

4. The process of claim 1, wherein the gel or cream base is a hydrated gel or cream base.

5. The process of claim 4, wherein the hydrated gel or cream base is selected from the group consisting of hydrated carboxyvinyl polymer, hydrated hydroxypropyl-methyl cellulose and mixtures thereof.

6. The process of claim 1, wherein the pharmaceutical composition comprises menthol.

7. The process of claim 6, wherein the layer of highly volatile silicone or mixture of highly volatile silicones comprises menthol.

8. The process of claim 1, wherein the mass ratio is no greater than about 6:1.

9. The process of claim 1, wherein the mass ratio is no greater than about 5:1.

10. The process of claim 1, wherein the mass ratio is at least about 6:1.

* * * * *

UNITED STATES PATENT AND TRADEMARK OFFICE
CERTIFICATE OF CORRECTION

PATENT NO. : 10,441,660 B2
APPLICATION NO. : 15/688728
DATED : October 15, 2019
INVENTOR(S) : Endre Mikulásik et al.

It is certified that error appears in the above-identified patent and that said Letters Patent is hereby corrected as shown below:

On the Title Page

In Column 1, item (73), Assignee, Line 1, delete "GYOCYSZERGYAR" and insert --GYOGYSZERGYAR--.

In Column 2, item (57), Abstract, Lines 7-8, delete "decamethylpentacyclo-siloxane." and insert --decamethylpentacyclosiloxane.--.

In the Drawings

Figure 10:
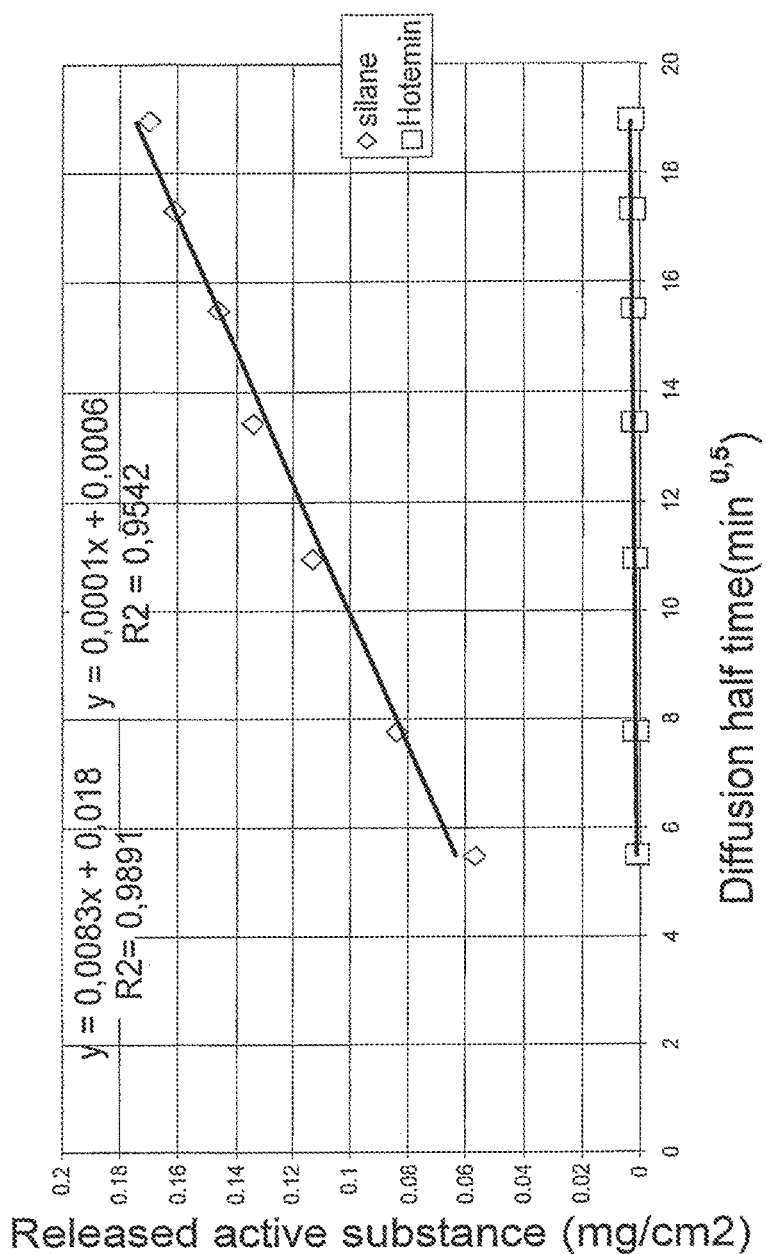
FIG. 10 relates to a comparative experiment, which demonstrates the release of piroxicam from the "silane system" and from Hotemin® composition through a semipolar membrane.

In sheet 10 of 11, FIG. 10, Line 1, delete "y=0,0083x + 0,018" and insert --y=0.0083x + 0.018--.

In sheet 10 of 11, FIG. 10, Line 1, delete "y=0,0001x + 0,0006" and insert --y=0.0001x + 0.0006--.

In sheet 10 of 11, FIG. 10, Line 2, delete "0,9891" and insert --0.9891--.

In sheet 10 of 11, FIG. 10, Line 2, delete "0,9542" and insert --0.9542--.

In sheet 10 of 11, FIG. 10, Line 13, delete "(min 0,5)" and insert --(min 0.5)--.

Figure 11:
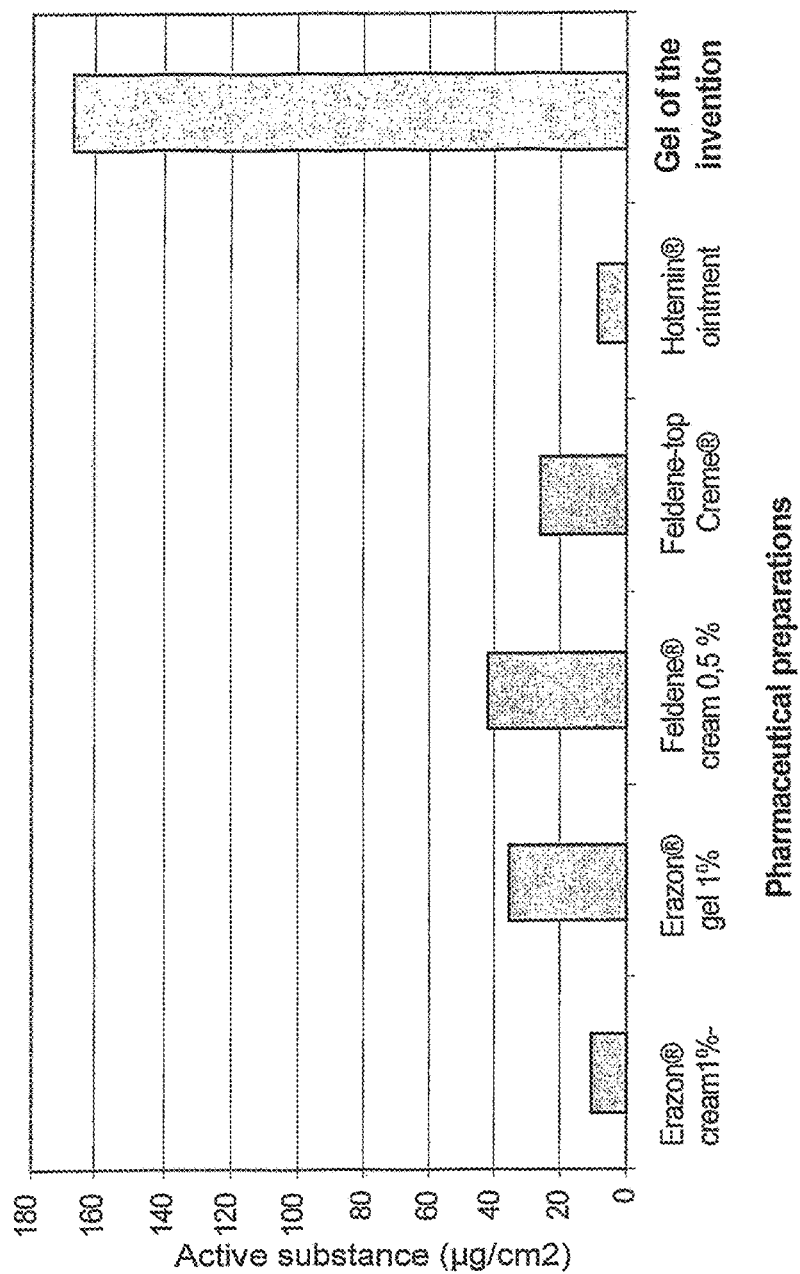
FIG. 11 relates to a comparative test, wherein the release of piroxicam from 6 different pharmaceutical preparations was studied. The diffusion time was 6 hours.

In sheet 11 of 11, FIG. 11, Line 12, delete "0,5%" and insert --0.5%--.

In the Specification

Column 2, Line 3, delete "hexamehyldisiloxane," and insert --hexamethyldisiloxane,--.

Column 2, Line 41, delete "bioavailabilty" and insert --bioavailability--.

Column 2, Line 61, delete "(metranidazol)." and insert --(metronidazol).--.

Signed and Sealed this
Twenty-eighth Day of January, 2020

Andrei Iancu
*Director of the United States Patent and Trademark Office*

Column 3, Line 6, delete "bioavailabilty" and insert --bioavailability--.

Column 5, Line 36, delete "stearil" and insert --stearyl--.

Column 5, Line 59, delete "Diffuson" and insert --Diffusion--.

Column 5, Line 67-Column 6, Line 1, delete "pharmacones" and insert --pharmaconex--.

Column 9, Line 35, delete "Metranidazol" and insert --Metronidazol--.